United States Patent [19]
Lindahl et al.

[11] Patent Number: 5,869,064
[45] Date of Patent: Feb. 9, 1999

[54] PROTEIN RIB, A CELL SURFACE PROTEIN THAT CONFERS IMMUNITY TO MANY STRAINS OF THE GROUP B STREPTOCOCCUS: PROCESS FOR PURIFICATION OF THE PROTEIN, REAGENT KIT AND PHARMACEUTICAL COMPOSITION

[75] Inventors: Gunnar Lindahl, Magnus Stenbocksgatan 5, S-222 24 Lund, Sweden; Margaretha Stalhammar-Carlemalm; Lars Stenberg, both of Lund, Sweden

[73] Assignee: Gunnar Lindahl, Lund, Sweden

[21] Appl. No.: 487,675

[22] Filed: Jun. 7, 1995

Related U.S. Application Data

[63] Continuation of PCT/SE94/00246 Mar. 21, 1994 published as WO94/21685 Sep. 29, 1994.

[30] Foreign Application Priority Data

Mar. 19, 1993 [WO] WIPO ..................... PCT/SE93/00234

[51] Int. Cl.⁶ ................................................... A61K 39/09
[52] U.S. Cl. ................ 424/244.1; 530/825; 435/253.4; 424/234.1
[58] Field of Search .............................. 424/190.1, 234.1, 424/244.1; 435/253.4; 530/387.9, 388.4, 389.5, 412, 825

[56] References Cited

U.S. PATENT DOCUMENTS

| | | | |
|---|---|---|---|
| 4,772,584 | 9/1988 | Cleary et al. | 514/2 |
| 5,302,386 | 4/1994 | Kasper et al. | 424/92 |
| 5,648,241 | 7/1997 | Michel et al. | 435/69.3 |

FOREIGN PATENT DOCUMENTS

| | | |
|---|---|---|
| 0367890 | 5/1990 | European Pat. Off. |
| 9104049 | 4/1991 | WIPO |
| 9217588 | 10/1992 | WIPO |

OTHER PUBLICATIONS

Baker et al., N. Engl. J. Med. 294:753–756 (1976).
Baker, J. Inf. Dis., 161:917–921 (1990).
Pritchard et al., Infect. Immun. 60:1598–1602 (1992).
Madoff et al, Infect. Immun., Jan, pp. 204–210, vol. 59(1), 1991.
Baker et al, J. Infect. Dis., Jul., vol. 154(1), pp. 47–54, 1986.
Baltimore, RS et al, J. of Immun, vol. 118(2), pp. 673–678, 1977.
Ferrieri, P, Reviews of Infect. Diseases, vol. 10, Supp. 2, Jul.–Aug., pp. S363–S366, 1988.
Michel, J.L. et al, Proc. Nat'l, Acad, Sci, USA, vol. 89, Nov., pp. 10060–10064, 1992.
Russell–Jones, G J et al, J. Exp. Med, Nov., vol. 160, pp. 1467–1475, 1984.
Salasia, S.I.O. et al, APMIS, vol. 102, pp. 925–930, 1994.
Wagner, A R et al, Infect. Immun, May, vol. 55(5), pp. 1170–1175, 1987.
Linden, ACTA path. microbiol. Immun. Scand. Sect. B, 91, pp. 145–151, 1983.
Lancefield, RC et al, J. of Exp. Med., vol. 142 pp. 165–179, 1975.
Mukasa, H. et al, Infect & Immun., vol. 7(4), pp. 578–585, 1973.
Flores, AE. et al, Zentralbl. Bakteriol. Mikrobiol, Hy8., vol.–259(2), pp. 165–178, Apr. 1985.
Lewin, Roger, Science, vol. 237, p. 1570, 1987.
Reeck et al, Cell, vol. 50, p. 667, Aug. 28, 1987.
Carberry–Goh et al, 1987, In:Streptococcal genetics, pp. 22–24.
Michel, James et al, pp. 214–218, In:Genetics and Molecular Biology of Streptococci, Lactococci, and Enterococci, 1991.
Coppel et al, In Methods in Molecular Biology, vol. 21, Antibody Screning of expression Libraries, pp. 277–296.

*Primary Examiner*—James C. Housel
*Assistant Examiner*—Ginny Allen Portner
*Attorney, Agent, or Firm*—Birch, Stewart, Kolasch & Birch, LLP

[57] ABSTRACT

This invention relates to a new protein, designated Rib, and subfragments, multiples or variants thereof, which confers protective immunity against infection with many group B streptococcal strains, in particular those of serotype III. The invention includes a procedure for purification of the protein, a procedure for preparation of highly specific antibodies, a reagent kit, a DNA sequence encoding the protein and a pharmaceutical composition comprising the protein or fragments or variants thereof.

24 Claims, 6 Drawing Sheets

Western blot analysis of 7 different λ clones.
Incubation with anti-Rib

Chromosomal Streptococcal DNA lane
1+8  λEcoRI/HindIII
2    BM110 DNA before CsCl 1µl
4    BM110 DNA after  CsCl 1µl
6    BM110 DNA Sau3AI        1µl λ Rib 3 DNA
(λ Maxi prep Promega)

lane
1  λEcoRI/HindIII
2  λRib 3
3  λRib 3 BamHI
4  λRib 3 SalI
5  λRib 3 PstI

PROTEIN RIB, A CELL SURFACE PROTEIN THAT CONFERS IMMUNITY TO MANY STRAINS OF THE GROUP B STREPTOCOCCUS: PROCESS FOR PURIFICATION OF THE PROTEIN, REAGENT KIT AND PHARMACEUTICAL COMPOSITION

This application is a continuation of PCT application No. PCT/SE94/00246 filed on 21 Mar. 1994, now WO94/21685, priority of which is claimed under 35 U.S.C. 120.

BACKGROUND AND FIELD OF THE INVENTION

This invention relates to a novel protein designated Rib (and subfragments, variants and multiples thereof) which confers immunity to most invasive straw of the group B Streptococcus, a procedure for purification of the protein, antibodies specific to the protein, a reagent kit and a pharmaceutical composition comprising the protein or fragments thereof.

During the last three decades, the group B Streptococcus has emerged as a major cause of neonatal disease in the Western world. In the United States alone, there are about 10,000 cases per year of invasive disease caused by this bacterium. These infections have an overall mortality of about 20%, and many of the infants that survive have permanent neurological sequelae. In view of these findings, a large effort has been made to find methods of prevention and treatment and to analyze the mechanisms by which group B streptococci cause infections.

About 20% of all women are vaginal carriers of the group B Streptococcus, and vertical transmission from the maternal genital tract is probably the most common source of infection in neonatal disease caused by this bacterium. However, only 1 to 2% of the infants that are colonized by the group B Streptococcus at birth are afflicted by serious infection. Other factors than exposure to the bacterium during birth must therefore contribute to the development of neonatal disease. Mothers of infected infants have significantly lower levels of antibodies to the type III capsule, which implies that these antibodies are important for protection against neonatal disease (Baker, C. J. and D. L. Kasper, N. Engl. J. Med. 1976, 294:753).

Group B streptococcal strains are divided into four major serotypes (Ia, Ib, II, and III) based on the structure of the polysaccharide capsule (Baker, J Inf Dis 1990. 161: 917). Serotypes I, II, and III occur in roughly equal proportions among strains in the normal flora, but type III accounts for about two-thirds of all isolates from invasive infections. Since the capsule is a known virulence factor, it has been studied in considerable detail, in particular in type III strains. Efforts have been made to develop a vaccine, in which the type III polysaccharide capsule would be an essential component. However, use of the polysaccharide capsule as a vaccine may give problems due to crossreactions with human tissues (Pritchard et al., Infect Immun 1992. 60: 1598). It would therefore be very valuable if one could develop a vaccine based on proteins rather than on polysaccharides.

The group B Streptococcus can also cause mastitis in cows, a bovine disease that is of considerable economical importance. Development of a vaccine against group B streptococcal infections is therefore of interest also in veterinary medicine.

Two group B streptococcal cell surface proteins have previously been studied in detail: the alpha and beta proteins. These proteins confer protective immunity to strains expressing the proteins, but they are of limited interest for group B streptococcal disease, since they are usually not expressed by type III strains, which cause the majority of serious infections.

SUMMARY OF THE INVENTION

The present invention, therefore, relates to a streptococcal cell surface protein, and variants and subfragments thereof. This protein, which is designated protein Rib, was isolated from a group B streptococcal strain of serotype III as a distinct 95 kD protein. Protein Rib is expressed by almost all group B streptococcal strains of serotype III and by a few strains of other serotypes such as II. A method has been devised to purify protein Rib and it has been demonstrated that antibodies to this protein protect against lethal infection with strains expressing protein Rib.

The invention also relates to naturally occurring and artificially modified variants, subfragments and multiples thereof with ability to protect against infections caused by protein Rib expressing bacteria, i.e. especially group B streptococcal strains of serotype III.

The invention also relates to a vector, such as a plasmid, a cosmid or a phage, containing the genetic code for protein Rib and variants, subfragments and fragments thereof, suitable for insertion in a non-human host organism and expression from said host. The invention particularly relates to three phage clones, lambda Ribl-3, lambda Ribl-5 and lambda Ribl-7, having deposit numbers DSM-9039, 9040, and 9041 respectively.

The invention also relates to a DNA sequence encoding protein Rib and variants, subfragments fragments and multiples thereof, that may be inserted in a suitable vector, such as a plasmid, a cosmid or a phage. The DNA sequence can be obtained from the deposited phages lambda Ribl-3, lambda Ribl-5 and lambda Ribl-7.

DETAILED DESCRIPTION OF THE INVENTION

Figure 1:
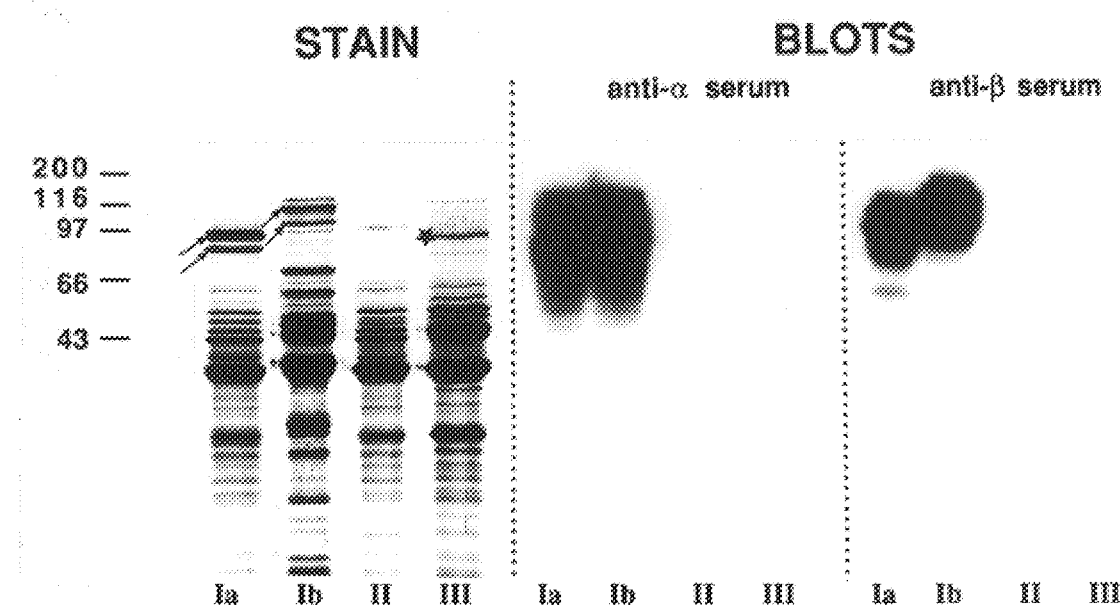

The Rib protein is expressed by different type strains. Extracts prepared from several different strains that were analyzed by Western blotting, using anti-Rib serum for the analysis, showed that almost all extracts contained protein Rib, but the molecular mass of the protein varied between 65 and 125 kD (data not shown). This result was not unexpected, since size variation has previously been described also for other group B streptococcal proteins, the alpha and beta proteins.

The available data suggest that the protein may consist of multiples of units, each unit corresponding to a molecular mass of about 9 kD. The invention therefore includes subfragments and multiples of the 95 kD protein or of a basic unit with the same characteristics. Variants include substitution or insertions of amino acids without changing the ability to protect against infections caused by bacterias expressing the protein.

Group B streptococcal strains are well known and may be isolated from the blood of infected human beings. The BM110 strain used by the inventors was obtained from Dr. S. Mattingly (University of Texas, San Antonio, Tex.). All strains referred to herein are obtainable from the inventors at the University of Lund and the Lund University Hospital (Doctor Gunnar Lindahl, Department of Medical Microbiology, Sölvegatan 23, S 22362 Lund, Sweden).

Protein Rib may be isolated from group B streptococcal strains of serotype III, preferably from strain BS30 or BM110. The invention concerns a process for purification of protein Rib.

The protein may be isolated by the following procedure: A Streptococcus Group B strain expressing the protein is cultivated, the medium and/or the microorganism are isolated, the bacteria are digested with an enzyme, preferably mutanolysin, a protease inhibitor is optionaly added, the digested bacteria are separated from the supernatant and protein Rib is extracted from the supernatant. The media can be any media suitable for cultivation of streptococci, such as Todd-Hewitt broth (Oxoid) and the cells are preferably cultivated 1–30, especially 12–20 hours. The digestion with an enzyme, preferably mutanolysin, is performed without shaking for 1–30, especially 1–20, preferably 15–18 hours at 20°–40° C., preferably 37° C. The protein may be isolated from the medium, and in such a case there is no need for digestion with the enzyme which is used to break the cell walls. A protease inhibitor such as benzamidine chloride, iodoacetic acid or phenylmethyl sulfonyl fluoride is added to prevent the action from proteases which may contaminate the mutanolysin or may be present in the microorganisms.

The protein can be purified by ion exchange chromatography, preferably anion exchange chromatography and gel filtration, and fractions containing the protein collected according to established practice within the art.

The invention especially concerns a substantially pure protein Rib or subfragments thereof. With the expression "substantially pure" we understand a substance that does not contain pharmaceutically harmful substances.

The invention also concerns antibodies-corresponding to protein Rib and subfragments, variants or multiples thereof. It is well known how to immunize an animal with an antigen, in this case protein Rib, collect the blood, isolate the serum and use the antibodies that react with the protein. The serum or an IgG fraction containing the antibodies may be used in analyzing the protein.

Since antibodies to protein Rib can protect against lethal infection with group B streptococcal strains, a method to measure the level of such antibodies can be valuable, for example in order to estimate if a pregnant woman has antibodies enough to protect the baby from such an infection. Protein Rib or subfragments thereof can be used to detect such antibodies to the protein. The invention therefore also concerns a reagent kit containing protein Rib or subfragments thereof.

It can also be of interest to analyze various samples for the presence of protein Rib. Antibodies to the protein can be used for this purpose. The invention therefore also concerns a reagent kit, comprising antibodies to protein Rib or subfragments thereof, for detection of the protein. A reagent kit may contain any of the above mentioned blood fractions containing the antibodies. It may also contain the protein, subfragments or multiples thereof for use as a standard.

The properties of protein Rib indicate that this protein can be used for the development of a vaccine against the group B Streptococcus. The invention therefore also concerns a pharmaceutical composition comprising the protein or fragments thereof as active ingredients, possibly together with pharmaceutically acceptable adjuvants and excipients. Suitable pharmaceutically acceptable adjuvants are those conventionally used in this field. Examples of suitable excipients are mannitol, lactose, starch, cellulose, glucose, etc., only to mention a few. The examples given of the adjuvant and the excipients are not to be regarded as limiting the invention.

The invention will now be described in more detail, with the accompanying drawings, in which:

FIG. 1 shows a Western blot analysis of extracts prepared from group B streptococcal strains representing the four main serotypes (type Ia: strain A909; type Ib: SB35; type II: B1284; type III: BS30). As shown in the immunoblot, the strains of types Ia and Ib express the alpha and beta proteins, and the positions of these proteins in the stained gel are indicated by arrows (lower arrow: alpha antigen; upper arrow: beta antigen). The position in the stained gel of the 95-kD protein Rib of the type III strain BS30 is indicated by a star. Molecular mass markers, indicated on the left, are in kD.

Figure 2A:
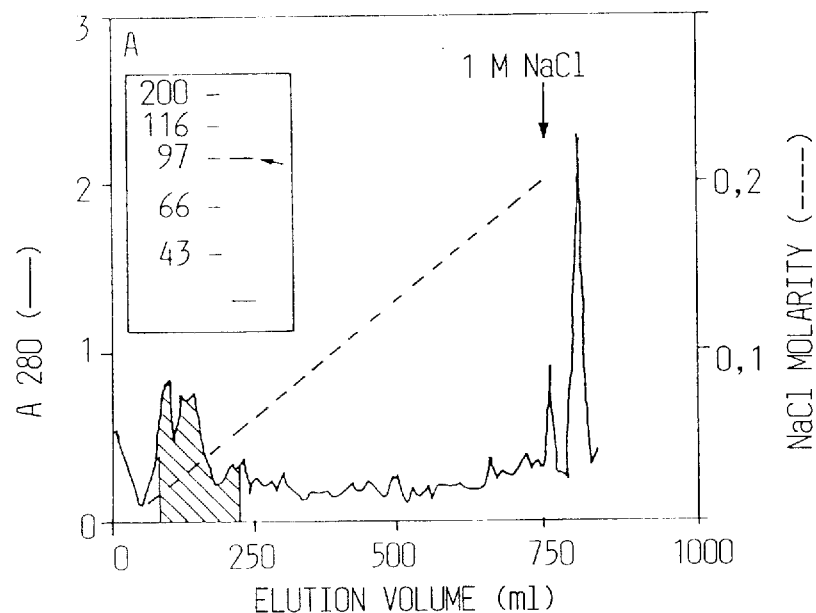
Figure 2B:
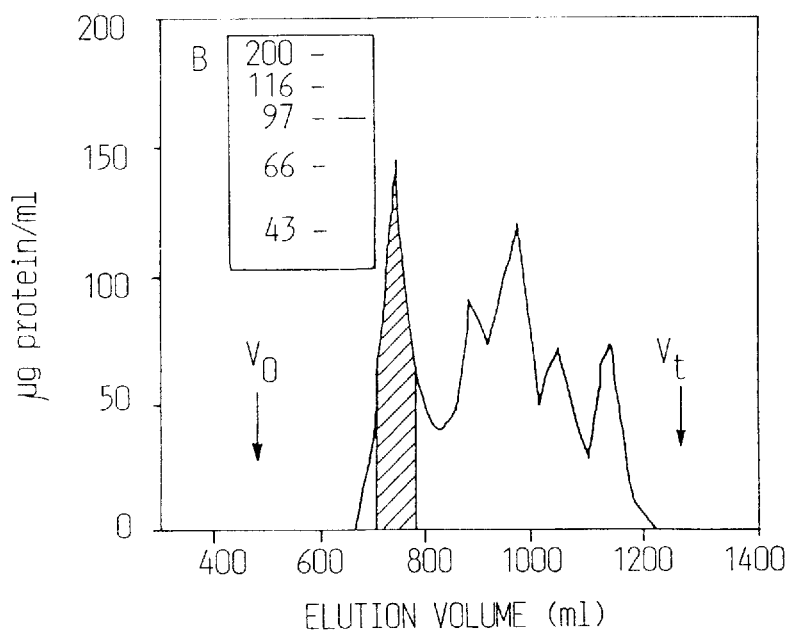

FIGS. 2A and 2B show purification of protein Rib from the type III strain BS30. (A) A mutanolysin extract, partially purified through a previous step of DEAE ion exchange chromatography, was subjected to ion exchange chromatography on a 30 ml column of DEAE Bio-Gel A, which was eluted with a linear gradient (800 ml) of NaCl in 10 mM Tris, pH 8.0, followed by 1M NaCl (60 ml). The shaded area indicates fractions containing protein Rib. The insert shows a pool of the protein Rib-containing fractions analyzed by SDS-PAGE; molecular mass markers, indicated on the left, are in kD, and the position of protein Rib (95 kD) is indicated by an arrow. (B) The pool of protein Rib-containing fractions from the ion exchange chromatography was subjected to gel filtration on a column (4.2×90 cm) of Sepharose CL6B. The shaded area indicates fractions containing protein Rib and the insert shows a pool of these fractions analyzed by SDS-PAGE. $V_0$, void volume; $V_t$, total volume.

Figure 3A:
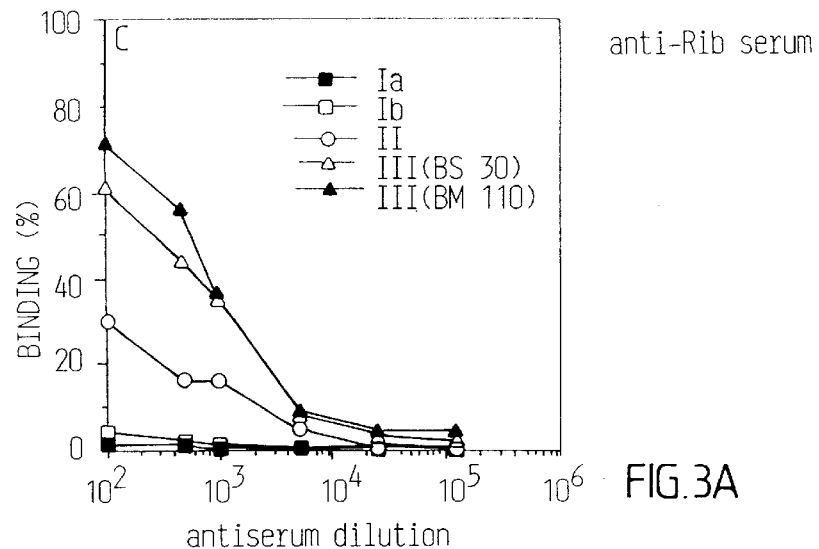
Figure 3B:
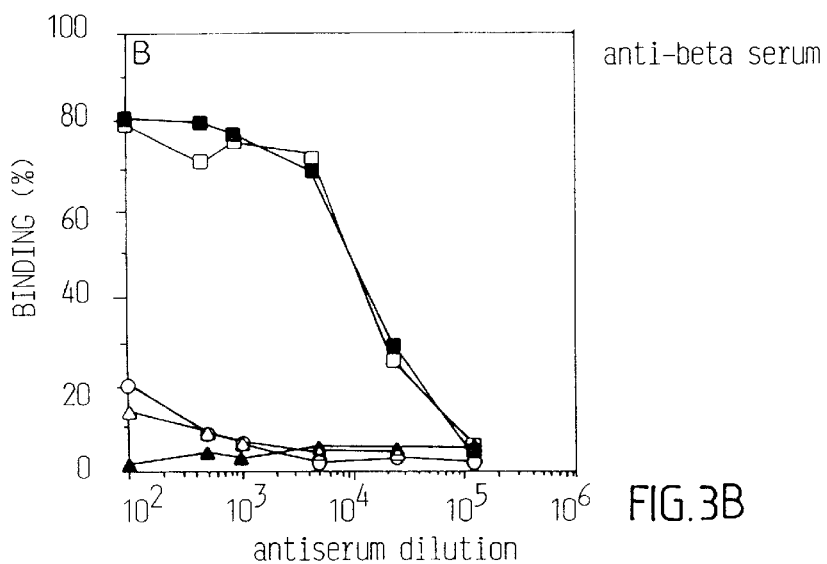
Figure 3C:
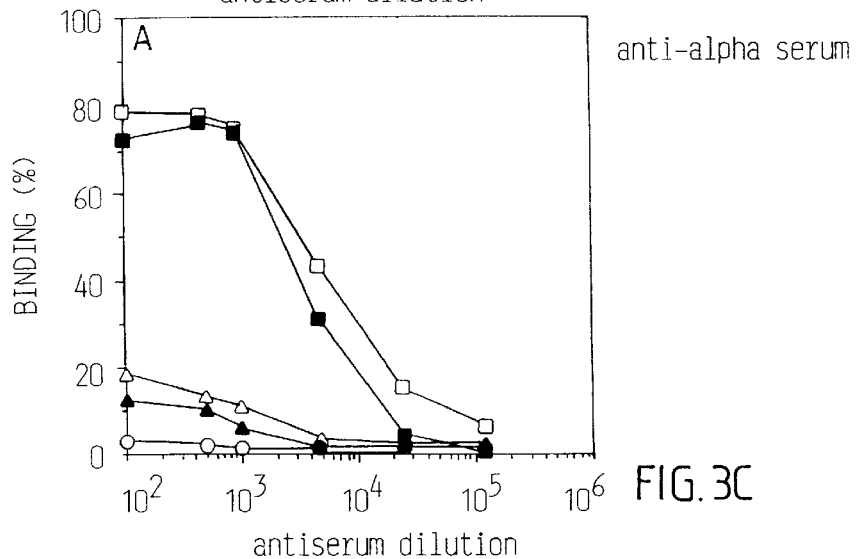

FIGS. 3A, 3B and 3C show analysis of group B streptococcal strains of the four major serotypes for cell surface expression of the alpha, beta and Rib proteins. Five strains were tested: A909 (type Ia); SB35 (type Ib); B1284 (type II); BS30 (type III), and BM110 (type III). The symbols used for these five strains are shown in panel C. Bacterial suspensions were incubated with different dilutions of rabbit antiserum to the alpha, beta, or Rib protein, as indicated. The numbers on the x-axis refer to final antibody dilution in the bacterial mixture. Bound antibodies were detected by incubation with radiolabelled protein G. Controls with preimmune rabbit serum were included in all experiments and were completely negative in all cases.

Figure 4:
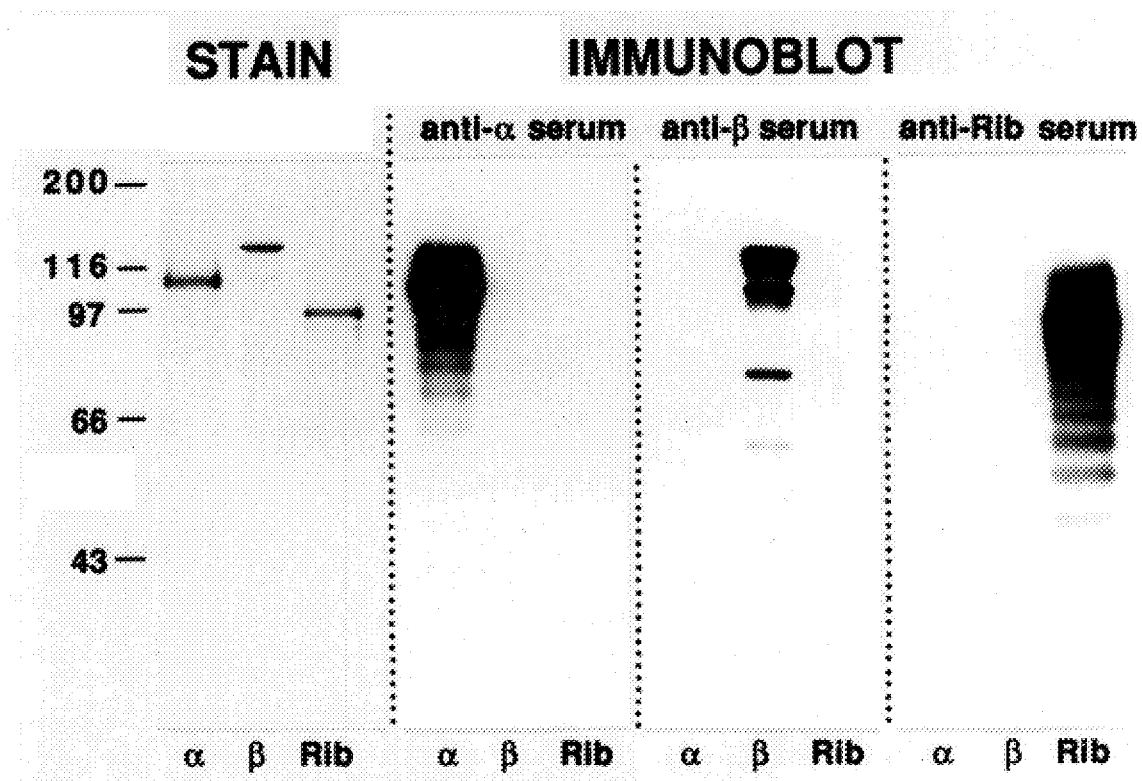

FIG. 4 shows Western blot analysis of purified alpha, beta, and Rib proteins with rabbit antisera raised against the purified proteins. Antisera were used at a 1:1,000 dilution, and bound antibodies were detected with radiolabelled protein G. Molecular mass markers, indicated on the left, are in kD.

Figure 5:
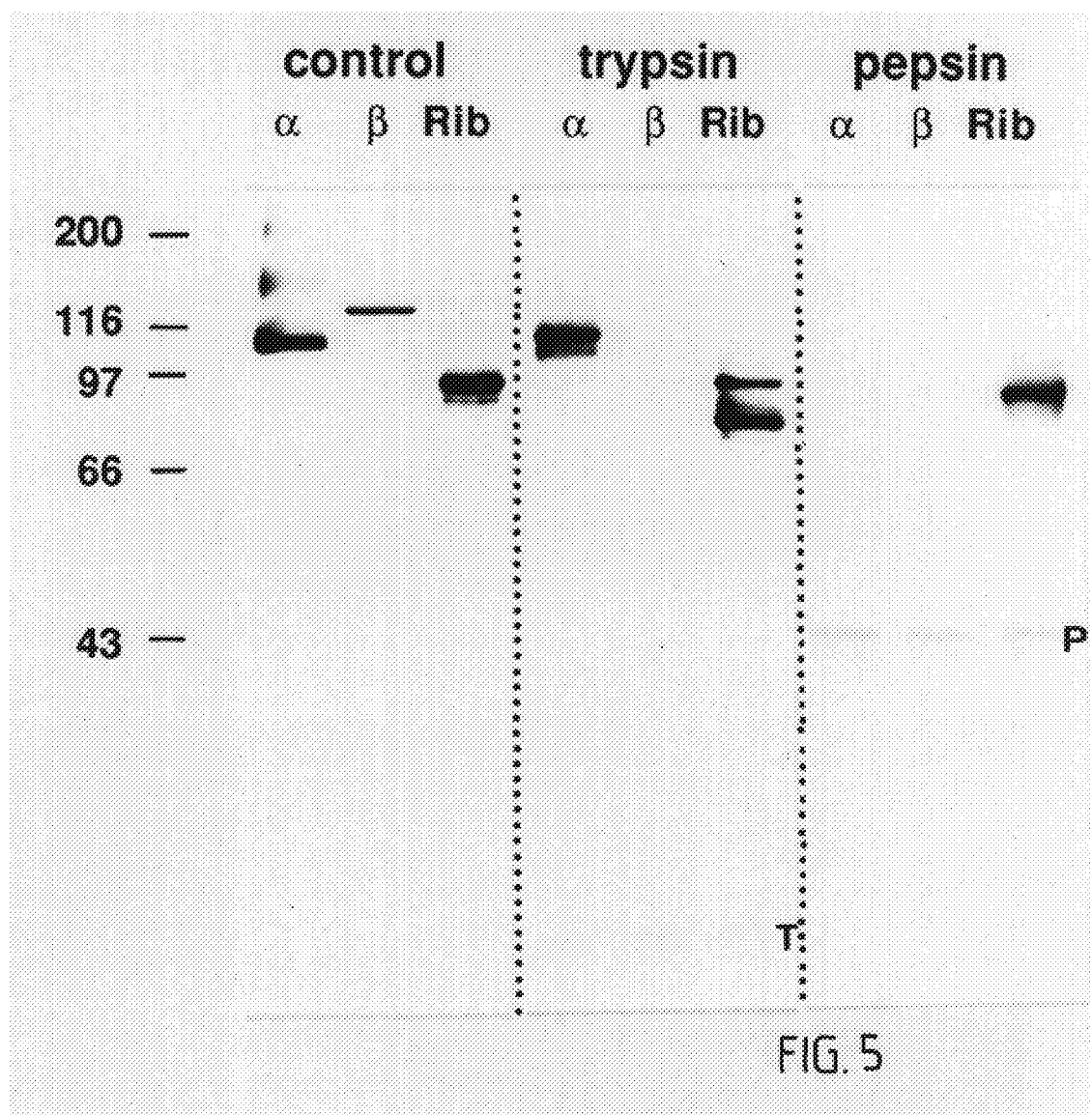

FIG. 5 shows SDS-PAGE analysis of the purified alpha, beta, and Rib proteins treated with trypsin or pepsin. The trypsin treatment was performed at pH 7.5, the pepsin treatment at pH 4.0. The samples were neutralized before the SDS-PAGE analysis. Controls were treated in the same way as the samples containing trypsin or pepsin, but no enzyme was added; such treatment did not cause degradation of the proteins. P=pepsin; T=trypsin. Molecular mass markers, indicated on the left, are in kD.

Figure 6A:
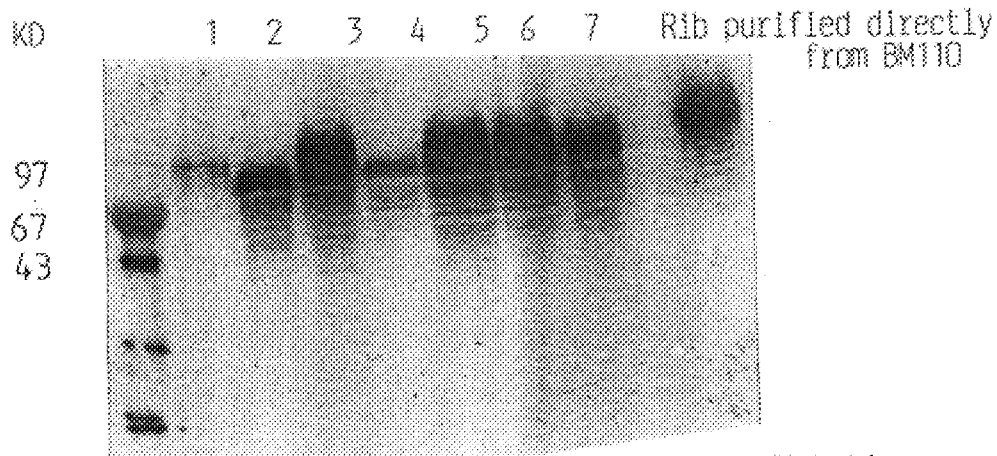
Figure 6B:
Figure 6C:
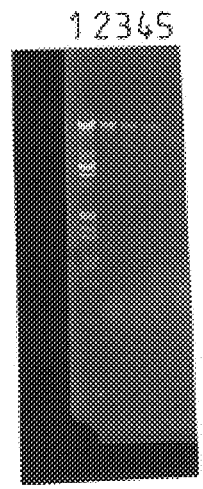

FIGS. 6A, 6B and 6C show the results of cloning of the rib-gene from strain BM110 and expression of protein Rib in *Escherichia coli*. (A) Western blot analysis of 7 different λ clones. Incubation with anti-Rib. (B) Restriction digests of chromosomal DNA from strain BM110. (C) Restriction digests of the Rib expressing λ-clone λrib3.

Mutanolysin extracts of several strains of different serotypes were analyzed by SDS-PAGE and by immunoblotting, using antisera to the alpha and beta proteins, see example 1. Results obtained with four strains representing the four major serotypes are shown in FIG. 1. The alpha and beta proteins, which are expressed by both the type Ia strain and the type Ib strain, gave rise to distinct bands in the high molecular weight region of the stained gel. These proteins vary in size between the two strains, in agreement with previous observations. A major protein species in the high molecular weight region was present also in the extract prepared from the type III strain, although this strain does not express the alpha protein or the beta protein. Such a distinct protein species of high molecular weight was also observed in extracts of other type III strains, and the protein appeared to vary in size between different strains. These similarities to the alpha and beta proteins made it of interest to study the high molecular weight proteins of type III strains in more detail. Strain BS30 was chosen for this work, because it was known to be mouse virulent. The 95-kD protein expressed by this strain (FIG. 1) was purified (Example 2) from mutanolysin extracts, using two consecutive steps of ion exchange chromatography, followed by gel filtration (FIG. 2). Fractions were analyzed by SDS-PAGE for presence of the 95-kD protein. When appropriate fractions from the gel filtration were pooled and analyzed, only two protein species were found: a major 95-kD protein and a minor 90-kD protein (see insert in FIG. 2B). The 90-kD protein most likely represents a degradation product of the 95-kD protein, since these two proteins were later shown to have the same $NH_2$-terminal sequence. The purified protein is referred to as protein Rib (resistance to proteases, immunity, group B). Antiserum to the 95-kD form of protein Rib was prepared by immunizing rabbits with slices cut out from SDS-PAGE gels.

To analyze whether protein Rib is a cell surface protein, strains representing the four major serotypes were tested for ability to bind anti-Rib serum (FIG. 3). The five strains studied included the four strains described above and an additional type III strain, BM110, which is a member of the high-virulence type III clone. For comparison, these five strains were also tested for expression of the alpha and beta proteins, using antisera to highly purified preparations of these proteins.

The anti-alpha serum reacted strongly with the Ia and Ib strains, as expected, and it also reacted weakly with the two strains of type III (FIG. 3C). However, mutanolysin extracts of the type III strains did not contain any detectable alpha protein, when analyzed in a Western blot. It therefore seems likely that this weak reactivity of anti-alpha serum with whole bacteria of type III represents a cross-reactivity with some other cell wall component. These data show that reactivity with anti-alpha serum can be used to unequivocally analyze whether a strain expresses the alpha antigen on the cell surface. Similar data were obtained with anti-beta serum (FIG. 3B).

The antiserum to protein Rib reacted with the two type III strains, but not with the type Ia and Ib strains (FIG. 3A). An intermediate level of binding was observed for the type II strain. When mutanolysin extracts of the five strains were analyzed in a Western blot experiment, using anti-Rib serum for the analysis, the extracts of the type III strains reacted strongly, giving major blotting bands at 95 kD, but the extracts of the three other strains completely lacked reactivity (data not shown). This result indicates that the intermediate reactivity of anti-Rib serum with the type II strain was due to a crossreactivity, which disappeared under the conditions of the Western blot. We conclude that protein Rib is expressed on the cell surface of the two type III strains, but not on the other three strains.

A total of 58 strains of known serotype, all of which had been isolated from invasive infections, were then tested for ability to bind antibodies to protein, Rib (see Table 1. example 6). Each strain was also tested for binding of antibodies to the alpha and beta proteins. To simplify the study of many strains, each antiserum was tested at a single 1000-fold dilution, chosen on the basis of the data shown in FIG. 3. This type of analysis gave unequivocal results, summarized in Table 1 of example 6. Protein Rib was found on the cell surface of 31 out of 33 type III strains and on one out of 13 type II strains, but not on any of the 12 strains of types Ia and Ib.

It seemed possible that strains lacking protein Rib on the cell surface excrete the protein into the medium. Culture supernatants of the 58 strains listed in Table 1 were therefore analyzed in a dot-blot experiment, using anti-Rib, serum for the analysis. Protein Rib was not detected in the supernatants of any of the 26 strains that do not express the protein on the cell surface, but was found in the supernatants of 26 of the 32 strains expressing the protein on the cell surface (data not shown).

A mouse protection model was used to study whether rabbit antibodies to protein Rib can protect against lethal infection with the group B Streptococcus (Table 2, Example 7). Control animals received antiserum to the alpha protein or preimmune serum, as indicated. The data show that antiserum to protein Rib protects mice against lethal infection with strains expressing protein Rib.

Since protein Rib confers protective immunity, like the alpha and beta proteins, it was of interest to compare these three proteins. A Western blot experiment was performed, using antisera to the purified proteins for the analysis (FIG. 4). The staining gel showed that the three proteins were highly purified, with one major species in each preparation, but there was no serological cross-reaction between the three proteins, as shown in the Western blot.

The alpha and beta proteins were originally distinguished due to a difference in protease sensitivity. The alpha protein is resistant to trypsin but sensitive to pepsin, while the beta protein is sensitive to both of these proteases (Bevanger and Maeland, *Acta Path Microbiol Scand Sect B* 1979, 87:51). An experiment with the purified alpha and beta proteins confirmed this difference and also demonstrated that protein Rib is resistant to both trypsin and pepsin (FIG. 5). As expected, all three proteins were sensitive to degradation by proteinase K (data not shown). The protease resistance of protein Rib was not due to the presence of an inhibitor, since beta protein was completely degraded by both trypsin and pepsin even in the presence of protein Rib (data not shown).

The invention will now be described with the following examples, which however do not limit the scope of the invention.

EXAMPLE 1, IDENTIFICATION OF THE PROTEIN

Four group B streptococcal strains representing the four main serotypes were used as reference strains: A909, type Ia/c; SB35, type Ib, B1284, type II; BS30, type III, described here. The BS30 strain was isolated at Lund University Hospital from a boy with neonatal infection. All bacterial strains were grown in Todd-Hewitt broth (Oxoid) at 37° C., without shaking. Mutanolysin extracts of the strains were analyzed by SDS-PAGE and by immunoblotting using antisera to the alpha and beta proteins. Small-scale mutanolysin extracts of streptococcal strains were prepared as described for the large-scale extracts used for protein purification, but cultures of only 50 ml were used to prepare 20% bacterial suspensions, of which 1 ml samples were digested with the enzyme.

SDS-PAGE was performed with standard techniques, using a total polyacrylamide concentration of 10% and a cross-linking of 3.3%. Samples were boiled for 3 min in a solution containing 2% SDS and 5% 2-mercaptoethanol prior to electrophoresis. The separated proteins were stained with Coomassie Brilliant Blue R-250 or transferred by electroblotting to a membrane of methanol-activated polyvinylidene difluoride (Immobilon-P; Millipore Corp., Molsheim, France), using a Semi-Dry Electroblotter (Ancos, Vig, Denmark). The Immobilon membranes were blocked with gelatin, using standard procedures, and then incubated with the indicated type of rabbit antiserum diluted 1000-fold (see example 7), followed by radiolabelled protein G and autoradiography.

Proteins were radiolabelled with carrier-free $^{125}I$ (Amersham International, England), using the chloramine T method. Total protein concentrations were determined with the MicroBCA protein assay reagent (Pierce). Electroelution of protein from SDS-PAGE gels was performed with a model 422 Electro-Eluter from Bio-Rad.

The results are shown in FIG. 1.

EXAMPLE 2, PURIFICATION OF PROTEIN Rib

The bacteria in a 10 l overnight culture of strain BS30 were spun down, washed twice with 50 mM Tris, pH 7.3, and resuspended to 20% (v/v) in the same buffer. Mutanolysin (Sigma Chemical Co., St. Louis, Mo.), dissolved to 5000 units/ml in 10 mM potassium phosphate, pH 6.2, was then added to the bacterial suspension (125 ml) to give a final concentration of 350 units/ml. The digestion was allowed to proceed for 17 h at 37° C. with gentle shaking, and protease inhibitors were then added to the following final concentrations; benzamidine chloride, 5 mM; iodoacetic acid, 5 mM; phenylmethyl sulfonyl fluoride, 2 mM. The suspension was centrifuged and the supernatant was immediately dialyzed (dialysis tubing Spectrapor No. 4) against 10 mM Tris, pH 8.0. This dialyzed preparation was subjected to two consecutive steps of ion exchange chromatography, which allowed the best recovery of pure protein Rib, as shown by preliminary experiments. The presence of protein Rib was analyzed by SDS-PAGE and visual inspection of the gels for the presence of the 95-kD band. In the first chromatography step, the dialyzed preparation (110 ml) was mixed with the same volume of 0.4M NaCl in 10 mM Tris, pH 8.0 and 30 ml of DEAE Bio-Gel A (BioRad Laboratories, Richmond, Calif.), equilibrated with 10 mM Tris, pH 8.0. The mixture was stirred gently at 4° C. for 1 h, and unabsorbed material (containing protein Rib) was freed from the gel by filtration through a glass filter. For the second chromatography step (FIG. 2A), the filtrate containing protein Rib was diluted twenty-fold with distilled water, to reduce the ionic strength, and mixed with 30 ml of DEAE Bio-Gel A, equilibrated as described above. After gentle stirring at 4° C. for 16 h, the gel was recovered by filtration and washed with 10 mM Tris, pH 8.0. Absorbed proteins (including protein Rib) were eluted with an 800 ml linear salt gradient (0–0.2M NaCl in 10 mM Tris, pH 8.0), followed by 1M NaCl (60 ml). Fractions (10 ml) were collected and those containing protein Rib were pooled, concentrated, and subjected to gel filtration in a column of Sepharose CL6B (4.2 cm×90 cm) in PBSA (0.12M NaCl, 0.03M phosphate, 0.02% $NaN_3$, pH 7.2) (FIG. 2B). The fractions were analyzed by SDS-PAGE electrophoresis for presence of the 95-kD band. Fractions (10 ml) containing protein Rib were pooled and frozen. The yield of protein Rib was about 6 mg from 25 g of bacteria. To ensure the purity of the protein Rib preparations used for immunochemical analysis, the protein used for such work was further purified by SDS-PAGE, followed by electroelution of the 95-kD band. However, SDS-PAGE analysis did not demonstrate any difference in purity between this electro-eluted material and that recovered from the gel filtration step.

As mentioned above, protein Rib is also found in the medium of strains expressing the protein. The protein can be purified from such a medium, using techniques similar to those described above.

Automated amino acid sequence analysis of protein bands transferred to Immobilon was performed directly on the membranes, using an Applied Biosystems 470A gas-liquid solid-phase sequenator. The membranes were lightly stained with Coomassie Brilliant Blue to localize the protein bands, which were then cut out for sequencing. The SwissProt Data Bank was used for analysis of protein sequences.

The $NH_2$-terminal sequence of protein Rib from strain BS30 is shown in SEQ ID NO:1. The two proteins with estimated molecular masses of 95 kD and 90 kD in purified protein Rib (FIG. 2B) were found to have the same $NH_2$-terminal sequence, suggesting that the smaller molecule is a degradation product of the larger one. A data search showed that the $NH_2$-terminal sequence of protein Rib is unique.

The same purification procedure was also followed for the isolation of protein Rib from strain BM110. The $NH_2$-terminal sequence (SEQ ID NO:2) of protein Rib isolated from strain BM110 may differ from the $NH_2$-terminal sequence of the corresponding protein from BS30 at position 7, where the BM110 protein may have Ser in place of Asp.

EXAMPLE 3, PURIFICATION OF THE ALPHA PROTEIN

The alpha protein was purified from strain SB35, a type Ib strain expressing both the alpha and beta proteins. The procedure used was similar to that used for purification of protein Rib from strain BS30. Fractions were analyzed for the presence of alpha protein by dot-blot analysis, using rabbit anti-alpha serum (kindly provided by Dr. L. Bevanger, University of Trondheim, Norway) and protein G (Calbiochem Co., San Diego, Calif.) radiolabelled with $^{125}I$. In the ion exchange and gel filtration steps, the behaviour of the alpha protein was similar to that of protein Rib (cf. FIG. 2). The alpha protein recovered from the gel filtration step was present in a sharp peak. Analysis of this material with different antisera indicated that it contained trace amounts of contaminating beta protein, which was removed by passage of the preparation through a small column of IgA-Sepharose. The purified alpha protein had a molecular weight of about 110,000, according to SDS-PAGE analysis (cf. FIG. 4). The yield of alpha protein was 12 mg from 39 g of bacteria. The alpha protein used for immunochemical work was further purified by electroelution from SDS-PAGE gels, as described above for protein Rib. However, SDS-PAGE analysis did not demonstrate any difference in purity between this electro-eluted material and that recovered from the gel filtration step.

EXAMPLE 4, PURIFICATION OF THE BETA PROTEIN

The IgA-binding beta protein (Russell-Jones et al, *J Exp Med* 1984. 160: 1467) was purified by a procedure similar to that used for the Rib and alpha proteins. The starting material was obtained by incubating washed SB35 bacteria in 50 mM glycine-NaOH buffer, pH 11.0 (final pH in suspension 9.7). Previous work in our laboratory had shown that the major protein species in such an extract is the beta protein. The extract (222 ml) was immediately dialyzed against 10 mM Tris, pH 8.0, diluted twenty-fold with distilled water and mixed with 40 ml of DEAE Bio-Gel A (equilibrated with 10 mM Tris, pH 8.0). After gentle stirring at 4° C. for 2 h, the gel was transferred to a column and eluted with an 800 ml linear salt gradient (0–0.2M NaCl in 10 mM Tris, pH 8.0). A dot blot procedure was used to test fractions (10 ml) for presence of beta protein, using radiolabelled IgA or anti-beta serum and radiolabelled protein G for the analysis. The beta protein was eluted in the first part of the gradient. Appropriate fractions were pooled, concentrated, and subjected to gel filtration on a column (4.2×100 cm) of AcA34 (Pharmacia-LKB, Uppsala, Sweden) in PBSA. The beta protein was eluted in a well-defined peak. Appropriate fractions were pooled, concentrated and frozen. The yield was 9 mg of pure protein from 23 g of bacteria. The major protein species in such a preparation had a molecular weight of about 130,000, according to SDS-PAGE, but small amounts of degradation products of lower molecular weight were also seen when the protein was subjected to Western blot analysis.

EXAMPLE 5, ANALYSIS OF PROTEASE SENSITIVITY

For analysis of protease sensitivity (FIG. 5), 200 $\mu$l samples of purified alpha, beta or Rib protein (0.5 mg/ml) were incubated for 1 h at 37° C. with trypsin, pepsin, or proteinase K (0.2 mg/ml). Trypsin digestion was performed in 0.25M sodium phosphate, ph 7.5, pepsin digestion in 0.25M sodium acetate, pH 4.0, and proteinase K digestion in 0.25M Tris, pH 7.4. The samples were neutralized before analysis by SDS-PAGE.

EXAMPLE 6, ANALYSTS OF STREPTOCOCCAL STRAINS FOR CELL SURFACE EXPRESSION OF THE ALPHA, BETA AND Rib PROTEINS

Five reference strains available in our laboratory were first analyzed for surface expression of the alpha, beta and Rib proteins. Later, a collection of 58 group B streptococcal strains, all isolated from cases of invasive infections, were also used to study the expression of these cell surface proteins (see Table 1). Typing of group B streptococcal strains was performed in the Clinical Microbiology Laboratory of Lund University Hospital, using standard techniques.

The bacteria in a 10 ml overnight culture were washed twice with PBSAT (PBSA supplemented with 0.05% Tween 20) and a 1% suspension in PBSAT was prepared. A sample (180 $\mu$l) of this bacterial suspension was mixed with 20 $\mu$l of rabbit antiserum that had been diluted in PBSAT and the mixture was incubated at 23° C. for 1 h. Two ml of PBSAT were then added, the bacteria were spun down, washed once with 2 ml of PBSAT, and resuspended in 200 $\mu$l of PBSAT. For detection of bound IgG, 25 $\mu$l of radiolabelled protein G (about $10^4$ cpm in PBSAT) was then added and incubation was continued at 23° C. for 1 h. Following addition of 2 ml of PBSAT, the bacteria were spun down and the pellet was then washed by addition of 2 ml of PBSAT. After a final centrifugation, the supernatant was discharged and the radioactivity in the pellet was determined. When many strains were tested for expression of the alpha, beta and Rib proteins (Table 1), a single final antiserum dilution of 1:1,000 was used. Controls with preimmune rabbit antiserum were always included and were completely negative in all cases. Protein Rib was found on the cell surface of 31 out of 33 type III strains, but not on any of the 12 strains of types Ia and Ib.

TABLE 1

Cell surface expression of the alpha, beta and Rib proteins by 58 group B streptococcal strains isolated from patients with invasive infections*

| Protein expressed | Capsular type | | | |
|---|---|---|---|---|
| | Ia (n = 9) | Ib (n = 3) | II (n = 13) | III (n = 33) |
| alpha | 6 | 0 | 4 | 0 |
| beta | 1 | 0 | 0 | 0 |
| alpha and beta | 1 | 3 | 5 | 0 |
| Rib | 0 | 0 | 1 | 31 |
| none | 1 | 0 | 3 | 2 |

The cell surface expression of the alpha, beta, and Rib proteins was analyzed with specific antisera, and bound antibodies were detected with radiolabelled protein G, as shown in FIG. 3.
*The 58 strains studied here were all isolated from cases of invasive infections, but do not represent a random collection of such strains, since most of the type II strains were later added to the collection originally studied, which included only two type II strains.

EXAMPLE 7, PREPARATION OF ANTISERA AND MOUSE PROTECTION TESTS

All antisera were produced in rabbits, which were immunized s.c. on the back. For preparation of antiserum to protein Rib expressed by strain BS30, slices corresponding to several 95 kD bands in SDS-PAGE gels were cut out, divided into small pieces and mixed with complete Freund's adjuvant. For the initial immunization, six slices (about 60 $\mu$g of protein) in 1 ml of PBS were mixed with 1 ml of adjuvant. Three bands (30 $\mu$g of protein) were used for booster injections. The first booster was given after 4 weeks and 3 additional boosters were given with intervals of 2 weeks. The rabbit was then bled 3 times with intervals of 3 weeks; the serum obtained from these 3 bleedings was pooled and used for the experiments reported here. Antiserum to the alpha protein was prepared by the same procedure. The first sample of anti-alpha serum, used to analyze fractions during the purification, was obtained from Dr Lars Bevanger, Trondheim. Antiserum to the purified beta protein was available in our laboratory.

C3H/HeN mice, bred in our department, were used at an age of 10–20 weeks. The mice were injected i.p. with 0.5 ml of a rabbit serum diluted five-fold in PBS, and infected 4 h later by i.p. injection of 0.5 ml of log-phase bacteria diluted in Todd-Hewitt broth. The number of bacteria used, which was estimated to be the 90% lethal dose ($LD_{90}$), was $2\times10^6$ c.f.u. for strains BM110, BE210, and SB35sedl. and $2\times10^7$ c.f.u. for BS30 and L25. Dead animals were counted daily for 4 days. Control animals usually died within 24 h.

TABLE 2

Rabbit antiserum to protein Rib protects mice against lethal infection with group B streptococcal strains expressing this protein

| Strain | Capsular type | Relevant cell surface protein* | Mice surviving† after pretreatment with | | |
|---|---|---|---|---|---|
| | | | anti-Rib serum | anti-alpha serum | normal serum |
| BS30 | III | Rib | 29/32[1] | 1/15 | 4/20 |
| BM110 | III | Rib | 15/24[1] | 0/15 | 0/15 |
| L25 | III | — | 0/15 | 2/14 | n.d.[II] |

TABLE 2-continued

Rabbit antiserum to protein Rib protects mice against lethal infection with group B streptococcal strains expressing this protein

| Strain | Capsular type | Relevant cell surface protein* | Mice surviving† after pretreatment with | | |
|---|---|---|---|---|---|
| | | | anti-Rib serum | anti-alpha serum | normal serum |
| BE210 | II | Rib | 10/15[9] | 0/14 | n.d. |
| SB35sed 1 | Ib | alpha | 1/15 | 10/15** | n.d. |

C3H/HeN mice were injected i.p. with 0.1 ml of rabbit antiserum (diluted to 0.5 ml with PBS) and challenged 4 h later with an $LD_{90}$ dose of log-phase bacteria, diluted into 0.5 ml of Todd-Hewitt broth. The survival data were analysed by the chi-square test.
*Expression of protein Rib or the alpha protein, the two antigens relevant to these experiments
†No. of mice surviving for 4 days/total no. of infected mice
[1]$P < 0.001$ when compared to the controls receiving anti-alpha serum or normal serum
[11]n.d. = not determinated
[9]$P < 0.001$ when compared to the controls receiving anti-alpha serum
**$P < 0.01$ when compared to the controls receiving anti-Rib serum The data in Table 2 demonstrate that antiserum to protein Rib protects against lethal infection with BS30, the type III strain from which the protein had been purified. This protection is not unspecific, as shown by the experiments with control sera. The anti-Rib serum also protected against lethal infection with another type III strain, BM110, a member of the high-virulence clone of group B streptococcal strains (Musser et al., *Proc. Natl. Acad. Sci* USA 1989. 86: 4731) In contrast, the anti-Rib serum did not protect against infection with L25, one of the type III strains that do not express protein Rib (Table 1). The protective effect of anti-Rib serum was not limited to type III strains, as shown by the experiments with a type II strain expressing protein Rib. As expected, anti-Rib serum did not protect against a type Ib strain expressing the alpha antigen. Taken together, these data strongly suggest that protein Rib acts as a virulence factor in almost all type III strains and in some type II strains, i.e. in most group B streptococcal strains causing invasive infections.

EXAMPLE 8, CLONING OF THE rib-GENE AND EXPRESSION OF PROTEIN RIB IN *ESCHERICHIA COLI*

The structural gene for protein Rib was cloned from strain BM110, a serotype III strain which is a member of a high-virulence clone. Protein Rib expressed by this strain (SEQ ID NO:2) and protein Rib expressed by strain BS30 (SEQ ID NO:1) have similar size and $NH_2$-terminal sequence. A library of strain BM110 DNA in bacteriophage lambda was constructed. The bacteria in a 500 ml log-phase Todd-Hewitt culture of the strain BM110 were spun down. The pellet was frozen and thawed 3 times, suspended in 20 ml TE buffer (10 mM Tris, 1 mM EDTA pH 8.0), centrifugated, washed and resuspended in 4 ml of the same buffer. Mutanolysin (Sigma Chemical Co. St Louis, Mo., USA) dissolved to 5000 units/ml in 10 mM potassium phosphate, pH 6.2, was added to the bacterial suspension to give a final concentration of 500 units/ml. Lysozyme (Sigma) was added to a final concentration of 8 mg/ml, and the digestion was allowed to proceed for 3 h at 37° C. The bacterial cells were lysed by addition of 200 μl of 10% SDS and 500 μl Tween lysing mix (2% Tween-20, 50 mM Tris pH 8.0 and 60 mM EDTA), followed by another 200 μl of 10% SDS. The lysate was treated with proteinase K (Sigma, 100 μg/ml) for 19 h at 50° C., followed by repeated phenol and chloroform extractions. The DNA was precipitated with ethanol, dried in a SpeedVac concentrator (SAVAC) and dissolved in 4.5 ml TE buffer. The DNA was further purified by CsCl density gradient ultracentrifugation and dialysed against TE buffer. The DNA concentration was then approximately 2.5 μg/μl. This DNA was partially digested with Sau 3AI (Promega), and ligated to Bam HI-cleaved arms of λEMBL 3 (Statagene). The recombinant phage DNA was packaged in vitro using Gigapack II Gold Packaging Extract (Stratagene). The library was plated on the *E. coli* strain LE392 and screened for production of protein Rib with an immuno-blotting technique: plates with about 1000 plaques were covered with a nitrocellulosa membrane and left at 4° C. for 1 h. The membranes were removed, blocked, and incubated in buffer containing rabbit anti-Rib serum, diluted 50-fold. Positive plaques, i.e. those binding rabbit IgG, were detected by addition of peroxidase-labeled protein A (Sigma) (20 μg/ml) and the presence of peroxidase was visualized, using standard techniques. Seven independent Rib expressing lambda clones were isolated. Three of these clones, i.e. lambda Ribl-3, lambda Ribl-5 and lambda Ribl-7, were deposited at Deutsche Sammlung von Microorganismen with deposit numbers DSM 9039, 9040, and 9041 respectively. A preparation of DNA from the lambda Ribl-3 clone having a DNA concentration of about 0.5 μg/μl was also made. Lysates of these seven clones were subjected to Western immunoblot analysis, using anti-Rib serum (see FIG. 6). Several of the clones express protein Rib of the same size as protein Rib isolated directly from strain BM110.

We claim:

1. A purified protein designated Rib, wherein:
   a) it is obtained from a group B streptococcal strain and has an apparent molecular weight of 65–125 kilodaltons (kD);
   b) it is resistant to degradation by trypsin and pepsin;
   c) it has the N-terminal amino acid sequence according to SEQ ID NOS:1 or 2; and
   d) it confers protective immunity against group B streptococcal strains expressing the protein.

2. A protein according to claim 1 wherein the strain is strain BS30 or BM110 and the protein has an apparent molecular weight of about 95 kD, as determined by sodium dodecyl sulfate-polyacrylamide gel electrophoresis.

3. Isolated antibodies specific for protein Rib as defined in claim 1.

4. A reagent kit for detection of antibodies to protein Rib, comprising at least one container which comprises protein Rib as defined in claim 1.

5. A reagent kit for detection of protein Rib, wherein it comprises antibodies specific to the protein as defined in claim 1, and optionally protein Rib as a standard.

6. A pharmaceutical composition comprising protein Rib as defined in claim 1, said composition firer comprising a pharmaceutically acceptable adjuvant or excipient.

7. A vaccine comprising protein Rib as defined in claim 1, said vaccine further comprising a pharmaceutically acceptable adjuvant or excipient.

8. A process for isolating protein Rib as set forth in claim 1, comprising:
   cultivating a streptococcus Group B strain which expresses protein Rib;
   isolating the medium; and
   extracting the protein from the medium.

9. A vector containing a DNA sequence encoding protein Rib, wherein the vector's DNA sequence encoding protein Rib is contained in the phage lambda Ribl-3, having deposit number DSM 9039.

10. A vector containing a DNA sequence encoding protein Rib, wherein the vector's DNA sequence encoding protein Rib is contained in the phage lambda Ribl-5, having deposit number DSM 9040.

11. A vector containing a DNA sequence encoding protein Rib, wherein the vector's DNA sequence encoding protein Rib is contained in the of phage lambda Ribl-7, having deposit number DSM 9041.

12. Phage lambda Ribl-3, having deposit number DSM 9039.

13. Phage lambda Ribl-5, having deposit number DSM 9040.

14. Phage lambda Ribl-7, having deposit number DSM 9041.

15. A purified protein designated Rib, wherein:
   a) it is obtained from a group B streptococcal strain;
   b) it is resistant to degradation by trypsin and pepsin;
   c) it has the N-terminal amino acid sequence according to SEQ ID NOS:1 or 2;
   d) it confers protective immunity against group B streptococcal strains expressing the protein; and
   e) it has an apparent molecular weight of about 95 kD as determined by sodium dodecyl sulfate-polyacrylamide gel electrophoresis.

16. A reagent kit for detection of antibodies to protein Rib, comprising at least one container which comprises protein Rib as defined in claim 15.

17. A pharmaceutical composition comprising protein Rib as defined in claim 15, together with a pharmaceutically acceptable adjuvant or excipient.

18. A vaccine comprising protein Rib as defined in claim 15, together with a pharmaceutically acceptable adjuvant or excipient.

19. A process for isolating the protein Rib as set forth in claim 1, comprising:

cultivating a Streptococcus Group B strain which expresses the protein Rib;

isolating the medium and the microorganism together or isolating the microorganism alone;

digesting the microorganisms with an enzyme;

separating the microorganisms from a resulting supernatant;

extracting the protein Rib from the supernatant.

20. A process according to claim 19 in which the protein is extracted from the supernatant by dialysis, fractionation by ion-exchange chromatography and gel filtration.

21. A process according to claim 19, wherein the enzyme used for digesting the microorganism is mutanolysin.

22. A process according to claim 19, wherein the process additionally comprises a protease inhibitor.

23. As isolated DNA molecule encoding the Rib protein of claim 1 wherein said DNA molecule is obtained from lambda Rib clones having deposit numbers DSM 9039, DSM 9040 or DSM 9041.

24. A purified recombinant protein designated Rib wherein:

a) the DNA encoding it is obtained from group B streptococcal strains b) it is resistant to degradation by trypsin and pepsin;

c) it has the N-terminal amino acid sequence according to SEQ ID NOS:1 or 2;

d) it confers protective immunity against group B streptococcal strains expressing the protein; and e) it has an apparent molecular weight of about 95 kD as determined by sodium dodecyl sulfate-polyacrylamide gel electrophoresis.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein (iii) HYPOTHETICAL: NO (iv) ANTI-SENSE: NO (v) FRAGMENT TYPE: N-terminal (vi) ORIGINAL SOURCE:
  (A) ORGANISM: Streptococcus group B
  (B) STRAIN: BS30

(xi) SEQUENCE DESCRIPTION: SEQ ID NO:1:

```
Ala Glu Val Ile Ser Gly Asp Ala Val Thr Leu Asn
1               5                   10
```

(2) INFORMATION FOR SEQ ID NO:2:

(i) SEQUENCE CHARACTERISTICS:
  (A) LENGTH: 12 amino acids
  (B) TYPE: amino acid
  (C) STRANDEDNESS: single
  (D) TOPOLOGY: linear (ii) MOLECULE TYPE: protein (iii) HYPOTHETICAL: NO (v) FRAGMENT TYPE: N-terminal (vi) ORIGINAL SOURCE:
  (A) ORGANISM: Streptococcus group B
  (B) STRAIN: BM110

(xi) SEQUENCE DESCRIPTION: SEQ ID NO:2:

```
Ala Glu Val Ile Ser Gly Ser Ala Val Thr Leu Asn
1               5                   10
```